United States Patent [19]

Greening et al.

[11] Patent Number: 5,434,561

[45] Date of Patent: Jul. 18, 1995

[54] REMOTE AUDIO/VISUAL ALARM APPARATUS

[75] Inventors: J. M. Greening; Robert F. Prater, both of Wichita, Kans.

[73] Assignee: Master Hydrosystems, Inc., Wichita, Kans.

[21] Appl. No.: 149,459

[22] Filed: Nov. 9, 1993

[51] Int. Cl.⁶ .............................................. G08B 21/00
[52] U.S. Cl. ................................. 340/603; 340/693; 210/85; 210/96.2
[58] Field of Search .................. 340/603, 693; 210/85, 210/96.2

[56] References Cited

U.S. PATENT DOCUMENTS

| | | | |
|---|---|---|---|
| 4,708,791 | 11/1987 | Dillard, III | 210/96.2 |
| 4,806,912 | 2/1989 | Clack | 340/603 |
| 4,851,818 | 7/1989 | Brown et al. | 210/85 |
| 5,057,212 | 10/1991 | Burrows | 210/85 |
| 5,145,575 | 9/1992 | Burrows | 210/85 |

*Primary Examiner*—John K. Peng
*Assistant Examiner*—Edward Lefkowitz

*Attorney, Agent, or Firm*—Hovey, Williams, Timmons & Collins

[57] ABSTRACT

An audio-visual alarm apparatus is provided for use with a water quality monitor having a pair of monitor nodes across which electrical conditions are indicative of whether the measured water quality is inside or outside of an acceptable quality range. The apparatus includes an audio-visual alarm and a circuit for energizing the alarm when the electrical condition across the monitor nodes is indicative of a measured water quality falling outside the acceptable range. The circuit includes a first relay for maintaining the circuit in a normally open position, and for closing the circuit when the relay is connected to the monitor nodes and a voltage condition across the monitor nodes is indicative of a measured water quality outside the acceptable range. Further, for certain monitors, it is possible to bypass the first relay by connecting the circuit directly to the monitor nodes. A second relay is provided in the circuit for normally preventing the energization of the alarm, and for providing energization to the alarm when the voltage condition across the monitor nodes is indicative of a measured water quality outside the acceptable range.

7 Claims, 1 Drawing Sheet

REMOTE AUDIO/VISUAL ALARM APPARATUS

BACKGROUND OF THE INVENTION

1. Field of the Invention

The present invention relates to an audio-visual alarm apparatus for use with a water quality monitor in providing a detectable alarm when the water quality measured by the monitor falls outside of an acceptable quality range. More particularly, the invention relates to an audio-visual alarm apparatus that is adaptable for use with any of a number of different kinds of water quality monitors and which is positionable remote from the monitor to which it is connected.

2. Discussion of the Prior Art

It is conventional to employ reverse osmosis deionization of water for use in hospitals for specialized applications such as hemodialysis. Because the treated water comes into contact with the blood of a patient as the blood is processed in the dialysis equipment, it is necessary to provide "ultra-pure water" from which all potentially dangerous contaminants have been removed.

Numerous water treatment systems are known for processing water in order to obtain ultra-pure quality acceptable for use in conventional dialysis equipment. In addition, these systems and others include water quality monitors capable of measuring either the conductivity or resistivity of the water being processed in order to provide an indication of the water quality achieved by the treatment system in Because of the close communication between water used in hemodialysis and blood treated in the process, catastrophic consequences may result if the treatment system fails or the quality of the water delivered from the system falls outside of an acceptable quality range. Therefore, it is necessary to provide a system for warning the health professionals supervising the hemodialysis process when such conditions occur.

A known water quality monitor for use with a conventional treatment system includes a control unit at which it is possible to set an acceptable water quality range, and a pair of contacts across which electrical conditions are indicative of whether the measured water quality is inside or outside of the preset range. Thus, a means is provided on the monitor for signaling an alarm which may be connected to the contacts so that the alarm is energized when the measured quality falls outside the preset range.

In certain conventional monitors, an alarm is included on the apparatus, and provides a visual indication of the quality of water being delivered from the treatment system. Unfortunately, because water treatment systems are often stored in separate utility rooms of a hospital, they are frequently out of range of health professionals to whom the alarm would have significance. In addition, where only visual indicators are used, there is a possibility that the health professional will misinterpret the meaning of the indicator and assume that the water quality is within the acceptable range when the indicator is lit.

An alternate proposed solution to the need for an effective alarm is to connect the monitor to a centralized processing unit located at a remote location in the hospital, and to connect the processing unit to an alarm that is located in the vicinity of the dialysis equipment. However, this system is expensive and complex, and relies upon the dependability of the entire system in delivering the required alarm signal to the person standing over the dialysis equipment.

OBJECTS AND SUMMARY OF THE INVENTION

It is an object of the present invention to provide an audio-visual alarm apparatus that may be electrically coupled to the monitor of any of a number of different types of water treatment systems in order to provide an audio-visual alarm when the water being processed by the system falls outside of an acceptable quality range.

Further, it is an object of the invention to provide the alarm apparatus at a location remote from the treatment system and within the visual and audible range of health professionals supervising a dialysis process in which the treated water is being used so that the health professional receives an indication when the quality of the water being used in the process falls below an expected quality level.

It is yet another object of the invention to provide an alarm apparatus of simple construction which delivers reliable operation regardless of the type of monitor with which the alarm is coupled.

In accordance with these and other objects evident from the following description of a preferred embodiment, the invention relates to an audio-visual alarm apparatus for use with a water quality monitor having a means for measuring water quality, a means for setting an acceptable water quality range outside of which quality is unacceptable, and a pair of monitor nodes across which electrical conditions are indicative of whether the measured water quality is inside or outside the acceptable range.

The apparatus includes a housing that may be supported independent of and remote from the monitor, a visual indicator, an audio alarm, and a circuit for energizing the indicator and alarm when the electrical condition across the monitor nodes is indicative of a measured water quality falling outside the acceptable range. The circuit includes a first switching means for maintaining the circuit in a normally open position, and for closing the circuit when the first switching means is connected to the monitor nodes and a voltage condition across the monitor nodes is indicative of a measured water quality outside the acceptable range, and a bypass means in parallel with the first switching means for connecting the circuit directly to the monitor nodes when the first switching means is disconnected from the monitor nodes.

Power is supplied to the circuit of the inventive apparatus independent of the electrical conditions across the monitor nodes, and an on/off switch is provided for connecting and disconnecting power to the circuit. The circuit also includes a second switching means for normally preventing the energization of the indicator and alarm, and for providing energization to the indicator and alarm when the voltage condition across the monitor nodes is indicative of a measured water quality outside the acceptable range.

By providing an audio-visual alarm apparatus in accordance with the present invention, numerous advantages are achieved. For example, by providing both a first switching means and a bypass means, it is possible to use the apparatus with different types of monitors without requiring a substantial change in the circuitry of the apparatus.

When the apparatus is used with certain monitors, the first switching means is attached to the monitor nodes and receives a voltage across the nodes when the measured water quality falls outside of an acceptable range. Upon receiving this voltage, the circuit is closed and the indicator and alarm are energized.

Other types of monitors present nodes in the form of dry contacts which are decoupled from one another as long as the quality measured by the monitor is within an acceptable range, but which are coupled when the quality falls out of the range. When the alarm apparatus is used with this type of monitor, the bypass means is connected directly to the monitor nodes and bypasses the first switching means. In this manner, the bypass means closes the circuit when the monitor nodes are coupled so that the indicator and alarm are energized.

Thus, the apparatus of the present invention may be utilized with different treatment systems while providing the same reliable alarm function, and includes a housing which permits the apparatus to be positioned in the vicinity of health professionals to whom the alarm has significance.

BRIEF DESCRIPTION OF THE DRAWING FIGURES

A preferred embodiment of an audio-visual alarm apparatus constructed in accordance with the present invention is described in detail below with reference to the attached drawn figures, wherein.

DETAILED DESCRIPTION OF THE PREFERRED EMBODIMENT

Figure 1:
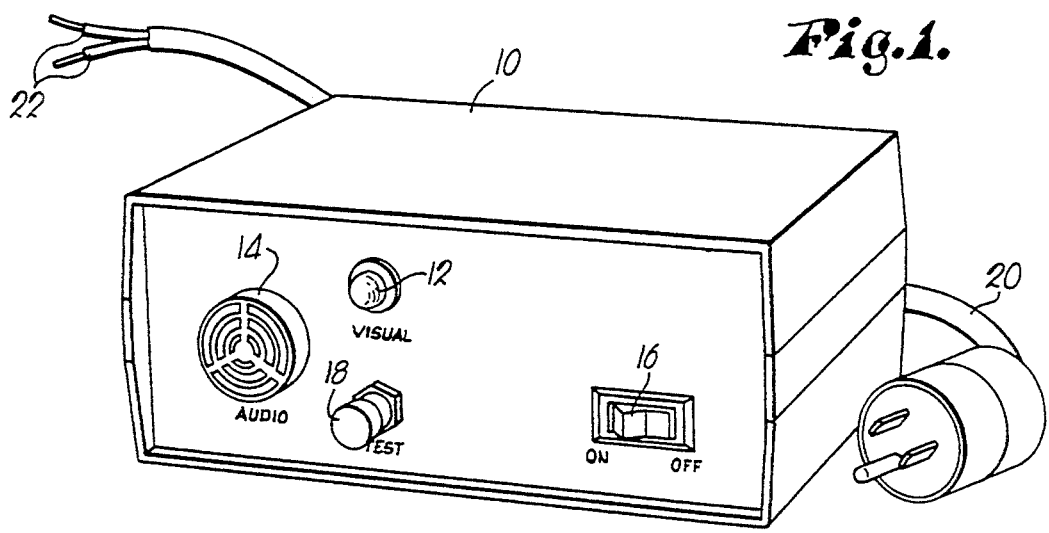
FIG. 1 is a prospective view of the audio-visual alarm apparatus.

An audio-visual alarm apparatus constructed in accordance with the preferred embodiment is illustrated in FIG. 1, and broadly includes a housing 10, a visual indicator 12, an audio alarm 14, an on/off switch 16, a test button 18, a power cord 20, and a pair of conductors 22.

The apparatus is designed for use in continuously monitoring the water quality in hemodialysis systems and other medical high purity water applications, and works in conjunction with most existing water quality monitors. For example, performance of the preferred embodiment has been proven on the following types of monitors: The SOLU METER brand direct reading ratio meter, produced by Beckman Industrial Corp.; the Type 822 Analog Indicator/Controller, produced by Thornton Associates, Inc.; the Model ROSLM 2120 System, produced by Continental Water Systems Corp.; and the Model 760 Series Conductivity Monitor, produced by Myron L. Company.

Each of these known monitors includes a means for measuring water quality, a means for setting an acceptable water quality range outside of which quality is unacceptable, and a pair of monitor nodes across which electrical conditions are indicative of whether the measured water quality is inside or outside the acceptable range. Some monitors provide a coupling across the monitor nodes and supply a voltage, commonly either 12 volts or 110 volts, when the measured quality value is outside the preset range. Other monitors provide a relay presenting a pair of dry contacts that are normally open, but which are closed when the relay is energized upon receipt of a signal indicative that the measured quality of the water is outside the desired range.

Figure 2:
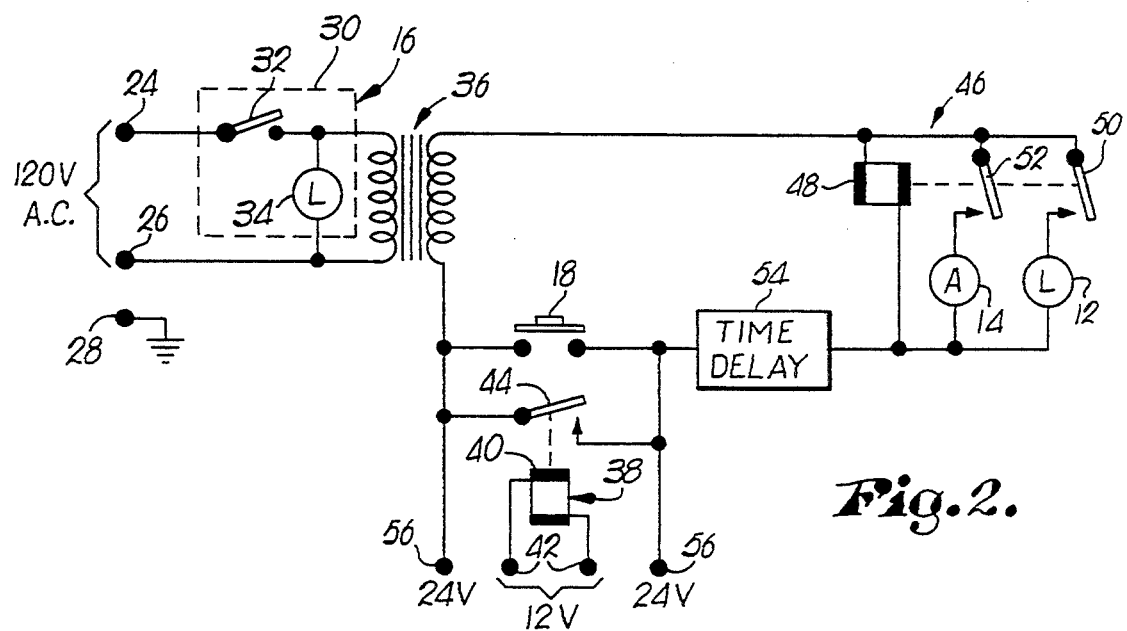
FIG. 2 is a circuit diagram of the apparatus.

As shown in FIG. 2, the alarm apparatus of the present invention incorporates a circuit that may be connected to either of these two types of monitors. The circuit includes the power cord 20, the switch 16, the test button 18, the visual indicator 12, the audio alarm 14, and other components to be described.

The power cord 20 is shown schematically as three nodes 24, 26, 28, and preferably includes a grounded plug of conventional construction which may be connected to any available AC power source. The switch 16 is depicted by the dashed line 30 as a lighted switch assembly including a switch contact 32 and a light 34 that is energized whenever the contact is closed. This provides an indication that the apparatus is turned on.

A transformer 36 is provided in the circuit for transforming the voltage of the AC power source to an output voltage appropriate for use by the circuit. For example, it is preferred to transform the voltage to a 24 volt output voltage, which may be either AC or DC.

The circuit also includes a first switching means 38 for maintaining the circuit in a normally open position, and for closing the circuit when the first switching means is connected to the monitor nodes and a voltage condition across the monitor nodes is indicative of a measured water quality outside the acceptable range. The first switching means 38 preferably includes a relay 40 presenting a pair of terminals that may be connected to the monitor nodes by the conductors 22, and a normally open contact 44 that is closed when the relay is energized.

A second switching means 46 is included in the circuit for normally preventing the energization of the indicator 12 and alarm 14, and for providing energization to the indicator and alarm when the voltage condition across the monitor nodes is indicative of a measured water quality outside the acceptable range. Preferably, the second switching means 46 includes a 24 volt relay 48 connected to the first switching means 38 and a pair of normally open contacts 50, 52 that are closed when the 24 volt relay is energized by closing of the circuit. The pair of normally open contacts 50, 52 are coupled to the indicator 12 and alarm 14 so that the indicator and alarm are energized when the contacts are closed.

Preferably, the circuit also includes a time delay means 54 for delaying energization of the indicator and alarm for a preset time period after the circuit is closed. Preferably, the time delay means includes an adjustable time delay unit having a rotatable delay adjustment mechanism and a pair of terminals for coupling the unit to the circuit. However, it is possible to provide a means having a fixed time delay so long as the delay is sufficient to allow for start up conditions within the water treatment system without triggering the alarm apparatus.

The test button 18 is arranged in parallel with the first switching means 38 so that when the test button is depressed, the circuit is closed and all of the components other than the first switching means are energized. It is noted that because of the presence of the time delay means 54 in the circuit, the test button must be depressed and held during the duration of the time delay before the indicator 12 and alarm 14 will be energized. This is necessary to test the operation of the time delay, as well as of the indicator and the alarm.

A bypass means is defined in the circuit in parallel with the first switching means 38 for connecting the circuit directly to the monitor nodes when the first switching means is disconnected from the monitor nodes. Preferably, the bypass means includes a pair of terminals 56 located in the circuit on either side of the first switching means. As described below, this bypass means is used to connect the apparatus to a monitor presenting a pair of normally open contacts that close when the measured quality falls outside of a preset range.

Figure 3:
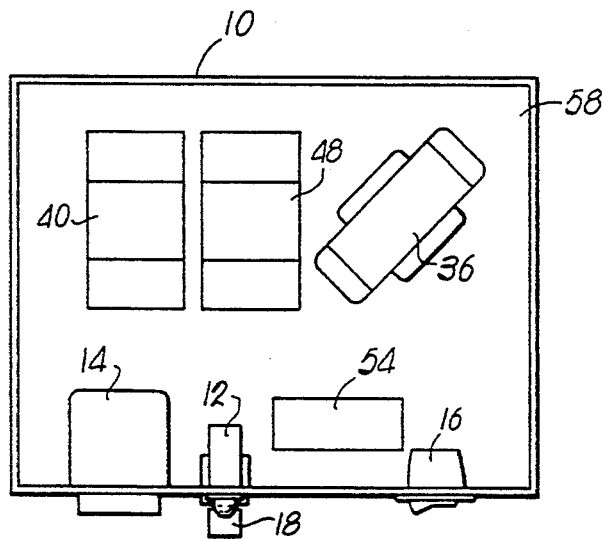
FIG. 3 is a schematic top plan view of the apparatus with a top cover of the housing removed to show the layout of the circuit components within the housing.

The physical arrangement of the various circuit components is shown in FIG. 3. Preferably, a floor panel 58 formed of electrically conductive material is provided in the housing 10 and supports the relays 40, 48, the transformer 36, and the delay means 54. Sockets may be provided on the panel for receiving the relays 40, 48 so that the relays may be replaced simply by pulling them from the sockets and inserting a different relay of either the same or a different voltage rating. The panel 58 is grounded through the power cord 20 to prevent accidental electrocution during handling of the apparatus.

The lighted switch 16, the test button 18, the visual indicator 12, and the audio alarm 14 are all supported on the front of the housing and are exposed for access and observation by users.

In order to describe operation of the apparatus, it is necessary to discuss the manner in which the circuit is connected to different types of monitors. Initially, setup of the circuit will be described with regard to a first type of monitor which presents a pair of nodes across which a voltage is supplied when the measured quality value is outside the preset range. When the apparatus is to be used with such a monitor, the nodes of the monitor are connected to the relay 40 at terminals 42 through the use of the insulated conductors 22.

The voltage required to energize the relay 40 of the first switching means 38 is the same as the voltage provided across the monitor nodes when the measured quality is substandard. For example, where the monitor voltage is 12 volts, the relay used in the first switching means 38 is a 12 volt relay. Likewise, if the monitor voltage is a voltage other than 12 volts, e.g. 110 volts, the relay used in the first switching means is of the same voltage rating.

In order to permit the apparatus to be used with all of the various monitors, regardless of the voltage provided across the monitor nodes, it is possible to permit replacement of the relay 40 of the first switching means 38 within the housing 10. Replacement of the relay 40 is achieved by employing relays that are uniform in construction such that any particular relay may be pulled from the housing and physically replaced by a different relay.

Once the relay 40 has been connected to the monitor nodes, the power cord 20 is coupled to a power source and the apparatus is ready for use. Typically, the apparatus is turned on at the same time as the water treatment system, and the time delay means 54 prevents the indicator 12 and alarm 14 from being energized during the period of time required by the system to bring the quality of treated water up to a preset standard. During initial setup of the apparatus, it is necessary to measure the length of this delay in the treatment system, and to adjust the time delay means accordingly. Thereafter, the time delay means will automatically delay energization of the indicator and alarm for the adjusted time period.

Assuming that the treatment system is operating properly upon conclusion of the delay period, no output voltage is delivered to the monitor nodes, and the contact 44 of the first switching means 38 remains open. Thus, no current is received by the relay 48 of the second switching means 46, and the indicator and alarm remain off.

If the measured water quality being processed in the treatment device falls outside of a desired range of values, the monitor generates a voltage across the monitor nodes. This voltage energizes the relay 40 of the first switching means 38, closing the contact 44 and the circuit. However, until the contact 44 has remained closed long enough to close the time delay means 54, the indicator and alarm remain off.

Once the contact of the first switching means has been closed for the period of time set by the delay means, current is delivered to the relay 48 of the second switching means 46 and energizes the relay to close the contacts 50, 52, lighting the indicator and sounding the alarm.

Setup of the circuit will now be described with regard to a second type of monitor which presents a relay including a pair of dry contacts that are normally open, but which are closed when the relay is energized upon receipt of a signal from the monitor indicative that the measured quality of the water is outside the desired range. When the apparatus is to be used with such a monitor, the nodes of the monitor are connected to the terminals 56 of the bypass means, which is embodied by a pair of terminals located in the circuit on either side of the first switching means. This connection is made by the same insulated conductors 22 as are employed with the first type of monitor described above.

Once the terminals 56 have been connected to the monitor nodes, the power cord 20 is coupled to a power source and the apparatus is ready for use. As with any other type of monitor, it is necessary during initial setup of the apparatus to measure the length of this delay in the treatment system, and to adjust the time delay means 54 accordingly.

Assuming that the treatment system is operating properly upon conclusion of the delay period, the monitor nodes remain open, as does the circuit. Thus, no current is received by the relay 48 of the second switching means, and the indicator and alarm remain off.

If the measured water quality being processed in the treatment device falls outside of the desired range, the monitor generates a voltage which energizes the monitor relay, closing the contact between the nodes. Thus, the circuit is closed. However, until the circuit has remained closed long enough to close the time delay means, the indicator and alarm remain off.

Once the contact of the monitor relay has been closed for the period of time set by the delay means, current is delivered to the relay 48 of the second switching means and energizes the relay to close the contacts 50, 52, lighting the indicator and sounding the alarm.

When the apparatus is used with this second type of monitor, the relay 40 of the first switching means 38 is bypassed, and it is not necessary to connect the relay to the nodes of the monitor. Likewise, when the first switching means is used to connect the circuit to a monitor of the first type described above, the terminals 56 are not attached to the monitor nodes.

Although the invention has been described with reference to the preferred embodiment illustrated in the attached drawing figures, it is noted that substitutions may be made and equivalents employed herein without departing from the scope of the invention as set forth in the claims.

What is claimed is:

1. An audio-visual alarm apparatus for use with at least first and second types of water quality monitors, wherein each type of water quality monitor includes a means for measuring water quality, a means for setting an acceptable water quality range outside of which quality is unacceptable, and a pair of monitor nodes across which electrical conditions are indicative of whether the measured water quality is inside or outside the acceptable range, the first type of water quality monitor including nodes across which a voltage is provided when the measured water quality is outside the acceptable range, the second type of water quality monitor including nodes that are closed when the measured water quality is outside the acceptable range, the apparatus comprising:

a housing independent of and remote from the monitor;

a visual indicator supported on the housing;

an audio alarm supported on the housing; and a circuit supported on the housing for energizing the indicator and alarm when the electrical condition across the monitor nodes of the selected type of water quality monitor is indicative of a measured water quality falling outside the acceptable range, the circuit including a first switching means for maintaining the circuit in a normally open position, and for closing the circuit when the first switching means is connected to the monitor nodes of the first type of monitor and a voltage condition across the monitor nodes is indicative of a measured water quality outside the acceptable range, a bypass means in parallel with the first switching means for alternately connecting the circuit to the monitor nodes of the second type of monitor when the first switching means is disconnected from the monitor nodes of the first type of monitor, a power supply means for supplying power to the circuit independent of the electrical conditions across the monitor nodes, an on/off switch for connecting and disconnecting power to the circuit, and a second switching means in the circuit for providing energization to the indicator and alarm when the voltage condition across the monitor nodes is indicative of a measured water quality outside the acceptable range.

2. An apparatus as recited in claim 1, wherein the circuit includes a testing means for manually closing the circuit and energizing the indicator and alarm to provide a test of the system.

3. An apparatus as recited in claim 1, wherein the circuit includes a delay means for delaying energization of the indicator and alarm for a preset time period after the circuit is closed.

4. An apparatus as recited in claim 1, wherein the first switching means includes a relay connected to the monitor nodes and a normally open contact that is closed when the relay is energized by electrical conditions across the monitor nodes.

5. An apparatus as recited in claim 1, wherein the power supply means includes a power input and a transformer for transforming the voltage of the power input into an output voltage, the on/off switch being connected between the power input and the transformer.

6. An apparatus as recited in claim 1, wherein the on/off switch includes a lighted indicator that is energized when the power is connected to the circuit in order to provide a visual indication that the apparatus is turned on.

7. An apparatus as recited in claim 1, wherein the second switching means includes a relay connected to the first switching means and a pair of normally open contacts that are closed when the relay is energized by closing of the first switching means, the pair of normally open contacts being coupled to the indicator and alarm so that the indicator and alarm are energized when the contacts are closed.

* * * * *